United States Patent [19]

DePrince et al.

[11] Patent Number: 4,765,980
[45] Date of Patent: Aug. 23, 1988

[54] STABILIZED PORCINE GROWTH HORMONE

[75] Inventors: Randolph B. DePrince; Ravi Viswanathan, both of Terre Haute, Ind.

[73] Assignee: International Minerals & Chemical Corp., Terre Haute, Ind.

[21] Appl. No.: 856,767

[22] Filed: Apr. 28, 1986

[51] Int. Cl.$^4$ .......................... A61K 35/55; A61F 2/00
[52] U.S. Cl. ...................... 424/108; 424/109; 424/423; 424/424; 424/425; 424/426; 514/6; 514/21; 514/776; 514/802; 514/964
[58] Field of Search ................. 514/6, 21, 2, 776, 802, 514/964; 424/108, 109, 423, 424, 425, 426

[56] References Cited

U.S. PATENT DOCUMENTS

| | | | |
|---|---|---|---|
| 1,181,424 | 5/1916 | Beveridge | 167/74 |
| 2,050,558 | 8/1936 | Bockmuhl et al. | 167/74 |
| 2,073,354 | 3/1937 | Schoeller et al. | 424/108 |
| 2,843,525 | 7/1958 | Robinson et al. | 167/75 |
| 2,902,408 | 9/1959 | Bouman et al. | 424/109 X |
| 3,239,418 | 3/1966 | Perlman | 424/109 X |
| 3,264,186 | 8/1966 | Parcells | 424/108 |
| 3,306,823 | 2/1967 | Choay et al. | 424/108 |
| 3,312,594 | 4/1967 | Norman et al. | 167/82 |
| 3,493,652 | 2/1970 | Hartman | 424/94 |
| 3,642,003 | 2/1972 | Kurtz | 128/335.5 |
| 3,664,925 | 5/1972 | Sonenberg et al. | 514/6 X |
| 3,867,520 | 2/1975 | Mori et al. | 424/36 |
| 4,003,846 | 1/1977 | Kuhn et al. | 252/316 |
| 4,046,871 | 9/1977 | Reckel | 424/11 |
| 4,054,558 | 10/1977 | Garsky | 260/112.5 |
| 4,059,694 | 11/1977 | Norton et al. | 424/177 |
| 4,101,649 | 7/1978 | Adam et al. | 424/12 |
| 4,107,288 | 8/1978 | Oppenheim et al. | 424/22 |
| 4,117,118 | 9/1978 | Hurri et al. | 424/177 |
| 4,130,554 | 12/1978 | Holly et al. | 260/112.5 |
| 4,146,611 | 3/1979 | Ondetti et al. | 424/177 |
| 4,357,259 | 11/1982 | Senyei et al. | 514/776 X |
| 4,371,523 | 2/1983 | Grodsky et al. | 424/178 |
| 4,390,527 | 6/1983 | Brantl et al. | 424/177 |
| 4,411,890 | 10/1983 | Momany | 424/177 |
| 4,427,659 | 1/1984 | Le Francier et al. | 424/177 |
| 4,439,424 | 3/1984 | Ecanow et al. | 424/153 |
| 4,450,150 | 5/1984 | Sidman | 424/1.1 |
| 4,452,782 | 6/1984 | Takemoto et al. | 424/177 |
| 4,503,035 | 3/1985 | Peetka et al. | 424/83 |

FOREIGN PATENT DOCUMENTS 2603321  8/1976  Fed. Rep. of Germany ...... 514/776

*Primary Examiner*—Thurman K. Page
*Attorney, Agent, or Firm*—Wendell R. Guffey; Thomas L. Farquer; George R. Repper

[57] ABSTRACT

Porcine serum albumin stabilizes porcine growth hormone, and provided for sustained release of porcine growth hormone in implant devices for swine.

21 Claims, No Drawings

STABILIZED PORCINE GROWTH HORMONE

BACKGROUND OF THE INVENTION

1. Field of the Invention

The invention relates to a method for stabilizing porcine growth hormone, and a stabilized porcine growth hormone composition.

2. Description of the Background Art

One major problem in the administration of growth hormones, such as porcine growth hormone administered to swine, is denaturation of the native globular structure causing aggregation of the growth hormone into precipitated forms which decreases the amount of active growth hormone available. The formation of these insolubles can also block tubing, membranes and various pumps of implanted delivery devices. System failure almost always results due to the formation of these insolubles. In addition to the formation of insolubles, another problem in the administration of growth hormones is retaining the soluble bioactivity of the hormone. It is therefore desirable to provide means for stabilizing growth hormone formulations in order to decrease the formation of insolubles and maintain the bioactivity of the soluble growth hormone.

A variety of stabilizers have been disclosed in the art which avoid the breakdown of native protein structures. For example, glycerol has been used to stabilize the activity of various proteins. Gekko, et al., *Biochemistry*, 20:4666-76 (1981). Examples of proteins which are described in this article as being stabilized by glycerol include chymotrypsinogen A (from bovine pancreas), ribonuclease A (from bovine pancreas), β-lactoglobin (from milk), bovine serum albumin, insulin (bovine pancreatic), egg-white lysozyme and α-chymotrypsin.

U.S. Pat. No. 4,179,337 discloses a process for coupling a polypeptide such as enzymes and insulin to polyethylene glycol or polypropylene glycol having a molecular weight of 500 to 20,000 daltons. The polyethylene glycol or polypropylene glycol is described as protecting the polypeptide from loss of activity and the composition can be injected without any immuniogenic response.

U.S. Pat. No. 4,439,181 discloses a method for preventing the precipitation of proteins within drug delivery systems that depend on the fluidity of the infusate for proper function. The method comprises mixing a polyol with the protein solution prior to introduction of the solution into the drug delivery system. Examples of the polyols which are described include glycerol and biocompatible C-4 to C-18 polyols. Exemplary of the polyols are erythritol, arabinose, xylose, ribose, adonitol, arabitol, rhamose, inositol, fructose, galactose, glucose, mannose, sorbose, maltose, sucrose, melezitose, and raffinose. The solid polyols are dissolved in a standard aqueous insulin solution or are first prepared as an aqueous solution and admixed with the insulin to provide the final concentration of polyol in the solution of about 10 to 90 percent weight per volume, with the balance being the protein. Other proteins which are described as being subject to the same precipitation problems include growth hormone, glucagon and the like.

While the prior art has taught a number of various stabilizers for specific proteins, unfortunately, the fact a particular stabilizer is effective with a particular protein does not necessarily mean that the particular stabilizer is appropriate for the stabilization of porcine growth hormone. Therefore, there exists a need for a method of stabilization of porcine growth hormone which decreases the formation of insolubles and preserves the soluble bioactivity of the hormone.

SUMMARY OF THE INVENTION

In accordance with the present invention, a method for stabilizing porcine growth hormone comprises admixing porcine growth hormone with a stabilizing amount of porcine serum albumin. Porcine serum albumin-stabilized porcine growth hormone compositions are also provided.

DETAILED DESCRIPTION OF THE PREFERRED EMBODIMENT

The present invention is directed to a method for the stabilization of porcine growth hormone (porcine somatotropin—sometimes referred to herein as pGH or simply as growth hormone), and a stabilized porcine growth hormone composition. According to the present invention, a stabilizing amount of porcine serum albumin (PSA) is mixed with porcine growth hormone prior to administration of the hormone to the animal. In one embodiment of the present invention, the stabilized growth hormone composition is an injectable formulation. In this embodiment, the stabilized growth hormone is in an aqueous solution comprising dissolved porcine growth hormone and dissolved porcine serum albumin. According to another embodiment of the present invention, the stabilized growth hormone is administered via an implant device. According to this embodiment, the stabilized growth hormone can be in a liquid or dry state. In a particularly preferred embodiment, an implant device is elected for the method of administration, and the stabilized growth hormone is in the form of a dry mixture comprising solid porcine growth hormone and solid porcine serum albumin which, upon implantation in an aqueous environment, become wetted and gradually dissolve.

As will be appreciated by those of skill in the art, the growth hormone may comprise a high weight percent of the overall weight of the stabilized growth hormone formulation when the formulation is in the solid state since water and other suitable aqueous solvents are not needed to enable the formulation to be injectable.

Porcine growth hormone for use in the present invention can be derived by known extraction and subsequent concentration techniques from the pituitary glands of swine. Porcine growth hormone produced by recombinant DNA methods are also suitable. The amino acid sequence of porcine growth hormone is known, and is described in an article by P. H. Seeburg et al., *DNA*, 2, 37, 45 (1983), (incorporated herein by reference). In addition to the above, one can also use modified porcine growth hormone that has up to about a dozen amino acid residues deleted from the amino end of the amino acid sequence of pGH. The pGH can also be in the form of a physiologically acceptable salt or metal complex thereof, such as Zn-pGH, Mn-pGH, Na-pGH and the like.

It has surprisingly been found that porcine serum albumin is an excellent stabilizer for porcine growth hormone, while also surprisingly providing outstanding sustained release characteristics for implant formulations. Porcine serum albumin is commercially available (e.g., from Sigma Chemical Co.), and has been found to stabilize porcine growth hormone when admixed there-with in respective ratio within the range of from about 10:1 to about 1:4, with a preferred ratio being about 4:1.

Advantageously, PSA is present in amounts sufficient such that when the PSA-pGH formulation is in an aqueous environment or solution, the solution is saturated with PSA. For injectable formulations, PSA should be from about 5% by weight up to total saturation in the aqueous formulation containing porcine growth hormone. For dry formulations, PSA may comprise higher weight percentages of the overall formulation since a major constituent, i.e., the water or aqueous solvent is eliminated.

The preparation of stabilized growth hormone formulations containing porcine serum albumin and porcine growth hormone may be by simple mechanical mixing. When an injectable form of the stabilized growth hormone formulation is desired, PSA is first dispersed in an aqueous solution which can be stirred or shakened to bring about a more rapid solubilization of the stabilizer. Porcine growth hormone is added after an aqueous solution of PSA has been formed. The weight percentage of the aqueous solvent or water need only be an amount sufficient to dissolve the PSA and growth hormone and to allow the formulation to be administered by injection. Amounts ranging from about 40 to about 90 percent by weight are believed to be suitable. While the above procedure has been described as being the preferred, the order of addition can be altered and should be in no way deemed as limiting to the scope of the present invention.

In another embodiment, the PSA and pGH can be co-lyophilized or dry mixed to provide a solid formulation which is particularly suited for implants. Dry composition according to this invention is suitable for storage and can later be admixed with fluid for injection. After the growth hormone and the PSA have been mixed, other optional additives, such as buffers, salts, adjuvants, and the like, may be added.

Since the present growth hormone formulations are intended to be administered to swine, the pH must be physiologically acceptable to the animal and not contribute to the destabilization of the growth hormone. Although it is anticipated that the pH of the stabilized growth hormone formulation may range from about 4 to about 10, the preferred pH range is from about 6.5 to about 8.0. The pH of the growth hormone formulation can be adjusted by effective amounts of a pharmaceutically acceptable base or acid to obtain the required pH. Suitable acids and bases are known to those skilled in the art.

This invention additionally provides a method for effecting growth promotion in swine which comprises administering to swine an effective amount of a stabilized growth hormone formulation comprising a growth promoting amount of porcine growth hormone with a stabilizing amount of porcine serum albumin.

The stabilized growth hormone formulations herein described can be administered to swine in a variety of ways. In one embodiment, the growth promoting formulation can be in a liquid form or solution which is administered by subcutaneous injection or via a liquid containing reservoir of an implanted delivery device.

In another embodiment, the stabilized growth hormone formulation is compressed into tablet or pellet form prior to being placed in a reservoir of a delivery device. Although a mixture consisting of porcine growth hormone and PSA alone can be pelletized or formed into tablets, various optional binders or other non-essential ingredients can be added to provide a formulation consisting essentially of PSA and pGH. Examples of binders which are suitable include sodium bentonite, ethyl cellulose, stearic acid, calcium stearate, adipic acid, fumaric acid, polyethylene glycol, deacetylated chitlon and cellulose acetate. The binder can be present in amounts which range from about 0.5 to about 10 percent by weight of the total weight of the solid stabilized growth hormone formulation. If desired, the binder can be present in amounts of from 1 to about 5 percent by weight.

Lubricants may also be added to the pellet to assist in the ease of manufacture. Examples of such lubricants include those common tablet water insoluble lubricants such as, for example, magnesium stearate, sodium stearate, calcium stearate, powdered stearate acid, talc, paraffin, cocoa butter, graphite, lycopodium, and the like, or combinations thereof. Normally, the lubricant is a fatty acid derivative such as the stearates, including magnesium stearate, sodium stearate, and calcium stearate. While the amount of lubricant may vary, the lubricant is generally present in amounts of from about 0.5 to about 10 percent by weight of the total weight of the pellet. If desired, the lubricant can be present in amounts of from about 1 to about 5 percent by weight.

A pelletized PSA-stabilized growth hormone formulation may be placed within the reservoir of an implantable delivery device. The reservoir is defined and surrounded by a wall, at least a portion of which comprises a porous membrane. The materials suitable for forming the porous part of the external wall of the device are generally those through which PSA and the growth hormone can pass by the process of diffusion. The pore size of the porous materials can be of from about 5 microns to about 250 microns, with 10 to 100 microns being preferred. Suitable materials for forming these walls are naturally occurring or synthetic materials that are biologically compatible with body fluids, tissues and organs and essentially insoluble in body fluids with which the device will come into contact. The use of materials soluble in body fluids is undesirable, since dissolution of the wall of the device would affect both the rate of release of the growth hormone and the capability of the system to remain in place for prolonged periods of time. The material also desirably is characterized by constant porosity; if the porosity changes over time the rate of release of the growth hormone also will change over time.

Materials suitable for forming the porous portion of the wall of the device are known in the art as having a plurality of fused particles which provide a supporting structure having microscopic sized interconnecting pores. A variety of such materials are commercially available or can be made by different methods known in the art, including etched nuclear track, leaching, polyelectrolytic processes, ion exchange polymer reactions and other techniques. See, for example, *Synthetic Polymer Membranes*, R. E. Kesting, Chapters 4 and 5, published by McGraw-Hill, 1971; and *Chemical Reviews: Ultrafiltration* 18:363–455 (1934).

Microporous materials useful for making these parts of the devices of the present invention include microporous polyalkylenes, such as microporous polyethylene, microporous polycarbonates, microporous polyamides, microporous modacrylic copolymers, polyesters prepared by esterification of a dicarboxylic acid or anhydride with an alkylene polyol, phenolic polyesters, cross-linked olefin polymers, polyolefins, polyurethanes, polyimides, and polybenzimidazoles. Preferred microporous materials are microporous polyethylene.

As one skilled in the art can appreciate, the rate of diffusion of the contents of the reservoir will depend upon the particular material, the ingredients of the reservoir, pore size of the porous material and the dimensions of the porous materials, i.e., thickness and surface area. While the present invention is not limited to any particular dimensions of the porous portion of the device, excellent results are achievable with microporous polyethylene discs having a pore size of from 10 to 70 microns, a diameter of 2 to 4 millimeters and thickness of 1.5 to 3 millimeters.

In the devices which can be advantageously used in connection with the present invention, typically only a portion of the external wall comprises a porous material. The remainder of the wall comprises a material that is essentially impermeable to the porcine growth hormone and PSA contained in the reservoir and to body fluids which are in contact with the implanted or inserted device. The impermeable portion of the external wall desirably is characterized much as the porous part of the wall was characterized above. The material should be compatible with body fluids, tissues and organs, and can comprise materials which are commercially available or can be made by processes known in the art. Suitable impermeable materials include steel or other suitable metals, acyl substituted cellulose acetates and alkyl derivatives thereof; partially and completely hydrolysed alkylene-vinyl acetate copolymers; unplastized polyvinyl acetate, cross-linked homo- and copolymers of polyvinyl acetate; cross-linked polyesters of acrylic and methacrylic acid, polyvinyl alkyl ethers, polyvinyl fluoride, silicone, polycarbonate, polyurethane, polyamide, polysulphones, polyimides, polyolefins, polybenzimidazoles; styrene acrlonitrile copolymers, cross-linked poly(ethylene oxide), poly(alkylenes), poly(vinyl imidazole), poly(esters), chlorosulphonated polyolefins and ethylene-vinyl ester copolymers such as ethylene-vinyl acetate. A preferred material is silicone.

Matrix implant systems, as are known in the art, are also suitable for use with PSA stabilized pGH.

The invention is illustrated by the following examples, which are not intended as limiting.

EXAMPLE 1

Zinc recombinant porcine growth hormone (Zn-rpGH—give source or microorganism strain) was sieved to a particle range of 250 to 75 microns and mixed by vortexing with porcine serum albumin (Sigma Chemical Co., fraction V, sieved to a particle range of 250 to 75 micron) in a 1:4 ratio. One hundred mg loads of the mixture were pelleted on a Key tableting machine using a 4 mm die.

Two of the 100 mg pellets were inserted into sterilized silicone tubing (ID 3.2 mm) with a 4 mm diameter teflon disk between them. Thirty-five micron MPPE (microporous polyethylene) disks (4 mm diameter, 1.5 mm length) were inserted into each end of the tubing until they abutted the pellets. The ends of the tubing were trimmed with a surgical blade, leaving a recessed end of 1.5 mm.

The above implant devices were implanted in swine, and performance of the implanted devices was compared to negative control (untreated swine) and positive control (swine injected with 2 mg Zn-rpGH/day for 25 days), in average daily gain (ADG), Average Daily Feed intake (ADF) and feed/gain (F/G) ratio over 25 days of study. The results are shown in Table 1 below.

TABLE 1

Data from Swine Study with Zn—rpGH

|  |  | negative control | positive control | Zn—rpGH/PSA Implant |
|---|---|---|---|---|
| 0–5 | ADG | 0.78 | 0.97 | 1.05* |
|  | ADF | 3.06 | 3.21 | 2.82 |
|  | F/G | 3.95 | 3.28 | 2.79* |
| 0–10 | ADG | 0.71 | 0.84 | 0.90 |
|  | ADF | 3.06 | 2.84 | 2.68 |
|  | F/G | 4.33 | 3.39 | 3.08* |
| 0–15 | ADG | 0.73 | 0.80 | 0.88 |
|  | ADF | 2.99 | 2.79 | 2.77 |
|  | F/G | 4.08 | 3.47 | 3.12* |
| 0–20 | ADG | 0.69 | 0.85 | 0.80 |
|  | ADF | 2.90 | 2.80 | 2.65 |
|  | F/G | 4.20 | 3.26 | 3.62 |
| 0–25 | ADG | 0.64 | 0.82* | 0.82* |
|  | ADF | 2.87 | 2.80 | 2.71 |
|  | F/G | 4.53 | 3.39** | 3.41** |

*Differs from mean of negative control ($P < .05$).
**Differs from mean of negative control ($P < 0.01$).

Swine treated with the above implants were superior to negative control, and were equivalent or superior to positive controls (2 mg Zn-rpGH/day injection for 25 days) in average daily gain and feed/gain ratio over the 25 days of the study.

EXAMPLE II

Recombinant porcine growth hormone (give source or microorganism strain) was sieved to a particle range of 250 to 75 microns and mixed by vortexing with porcine serum albumin (Sigma Chemical Co., fraction V, sieved to a particle range of 250 to 75 micron) in a 1:4 ratio. One hundred mg loads of the mixture were pelleted on the Key tableting machine using a 4 mm die.

Two of the 100 mg pellets were inserted into sterilized silicone tubing (ID 3.2 mm) with a 4 mm diameter teflon disk between them. Thirty-five micron MPPE (microporous polyethylene) disks (4 mm diameters, 1.5 mm length) were inserted into each end of the tubing until they abutted the pellets. The ends of the tubing were trimmed with a surgical blade, leaving a recessed end of 1.5 mm.

TABLE 2

Data from Swine Study with rpGH

|  |  | negative control | positive control | rpGH/PSA Implant |
|---|---|---|---|---|
| 0–5 | ADG | 0.84 | 0.91 | 0.70 |
|  | ADF | 2.82 | 2.57 | 2.45* |
|  | F/G | 3.49 | 3.27 | 3.53 |
| 0–10 | ADG | 0.78 | 0.92* | 0.79 |
|  | ADF | 2.87 | 2.62* | 2.47* |
|  | F/G | 4.04 | 2.94* | 3.16* |

*Differs from mean of negative control ($P < .10$).

Swine treated with the above implants were equivalent or superior to positive controls (2 mg rpGH/day injection) in reducing feed intake and near equivalent in feed/gain ratio for 10 days.

What is claimed is:

1. A method for stabilizing porcine growth hormone comprising admixing porcine growth hormone or a physiologically acceptable metal complex thereof with a stabilizing amount of porcine serum albumin.

2. The method of claim 1 wherein said porcine serum albumin and porcine growth hormone or a physiologically acceptable metal complex thereof are admixed in a respective ratio of from about 10:1 to about 1:4.

3. The method of claim 2 wherein said ratio is about 4:1.

4. A stabilized porcine growth hormone composition comprising a mixture of porcine growth hormone or a physiologically acceptable metal complex thereof and a stabilizing amount of porcine serum albumin.

5. The composition of claim 4 having a respective ratio by weight of porcine serum albumin to porcine growth hormone or a physiologically acceptable metal complex thereof of from about 10:1 to about 1:4.

6. The composition of claim 5 wherein said ratio is about 4:1.

7. An implantable delivery device for sustained release of stabilized porcine growth hormone containing the composition of claim 4.

8. An implantable delivery device for sustained release of stabilized porcine growth hormone containing the composition of claim 5.

9. An implantable delivery device for sustained release of stabilized porcine growth hormone containing the composition of claim 6.

10. An implantable delivery device comprising a physiologically acceptable, implantable porous container containing the composition of claim 4.

11. An implantable delivery device comprising a physiologically acceptable, implantable porous container containing the composition of claim 5.

12. An implantable delivery device comprising a physiologically acceptable, implantable porous container containing the composition of claim 6.

13. The composition of claim 4 in the form of a substantially dry pellet.

14. The composition of claim 5 in the form of a substantially dry pellet.

15. The composition of claim 6 in the form of a substantially dry pellet.

16. A method for promoting the growth of swine comprising administering to swine the composition of claim 4.

17. A method for promoting the growth of swine comprising administering to swine the composition of claim 5.

18. A method for promoting the growth of swine comprising administering to swine the composition of claim 6.

19. The method of claim 16 wherein said composition is administered in the form of a sustained release implant.

20. The method of claim 17 wherein said composition is administered in the form of a sustained release implant.

21. The method of claim 18 wherein said composition is administered in the form of a sustained release implant.

* * * * *